United States Patent [19]

Pernicka

[11] Patent Number: 5,303,428
[45] Date of Patent: Apr. 19, 1994

[54] COMBINATION OF A STRAP AND OF A STRAP SPREADER

[75] Inventor: Martin Pernicka, St. Francois, Laval, Canada

[73] Assignee: Leader Industries, Inc., Boucherville, Canada

[21] Appl. No.: 26,875

[22] Filed: Mar. 5, 1993

[51] Int. Cl.$^5$ .............................................. A61F 9/02
[52] U.S. Cl. .......................................... 2/452; 2/428; 351/156
[58] Field of Search ................ 2/2.1 R, 11, 425, 426, 2/428, 440, 441, 445, 452, DIG. 11, 430; 351/43, 155, 156; 128/201.27, 201.22, 205.25, 206.21, 207.17

[56] References Cited

U.S. PATENT DOCUMENTS

| | | | |
|---|---|---|---|
| 1,323,217 | 11/1919 | Darrow | 128/205.25 |
| 2,898,596 | 8/1959 | Keen | 2/425 |
| 2,993,209 | 7/1961 | Monahan, Jr. et al. | 2/428 |
| 4,077,068 | 3/1978 | Anderson | 2/428 |
| 4,264,987 | 5/1981 | Runckel | 2/445 |
| 4,468,819 | 9/1984 | Ohno | 351/43 |
| 5,046,200 | 9/1991 | Feder | 351/156 |
| 5,069,205 | 12/1991 | Urso | 128/206.21 |

Primary Examiner—Clifford D. Crowder
Assistant Examiner—Michael A. Neas
Attorney, Agent, or Firm—Omri M. Behr; Matthew J. McDonald

[57] ABSTRACT

The disclosure herein describes the combination of a strap and of a strap spreader for use in combination with goggles wherein the spreader is defined by a surface that fits the contour of the back of a wearer's head. The body includes points of attachment vertically distanced from one another on opposite sides of the body to spread the strap portions from one another at the back of the head. One application of such combination is its use by swimmers.

10 Claims, 3 Drawing Sheets

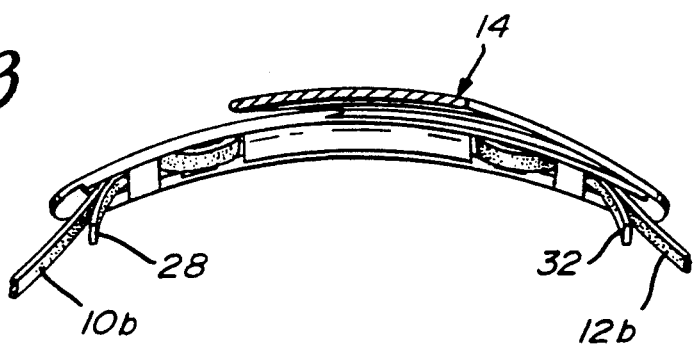
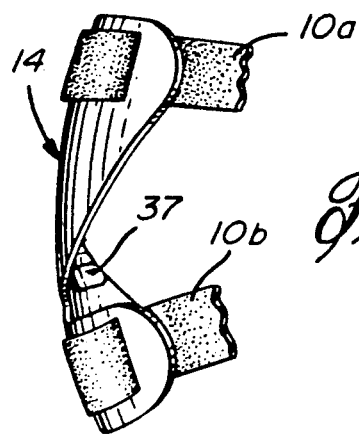
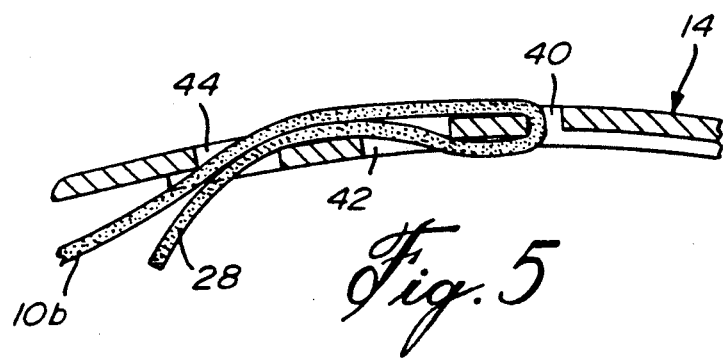
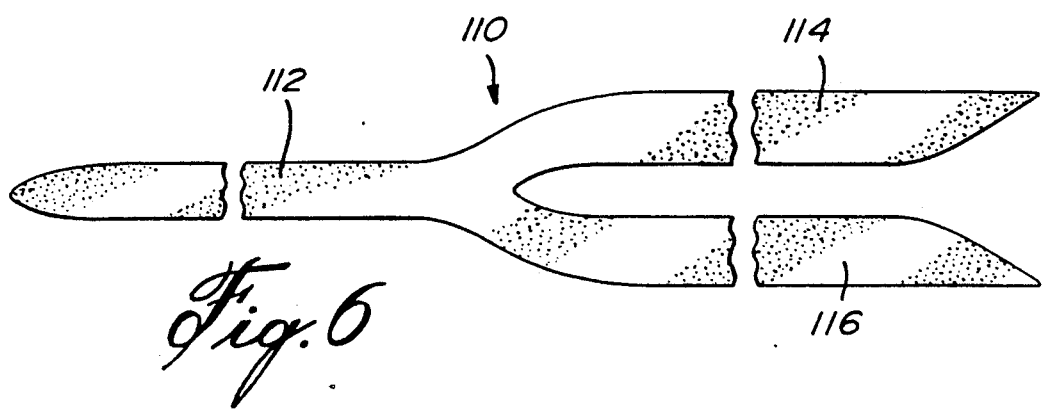

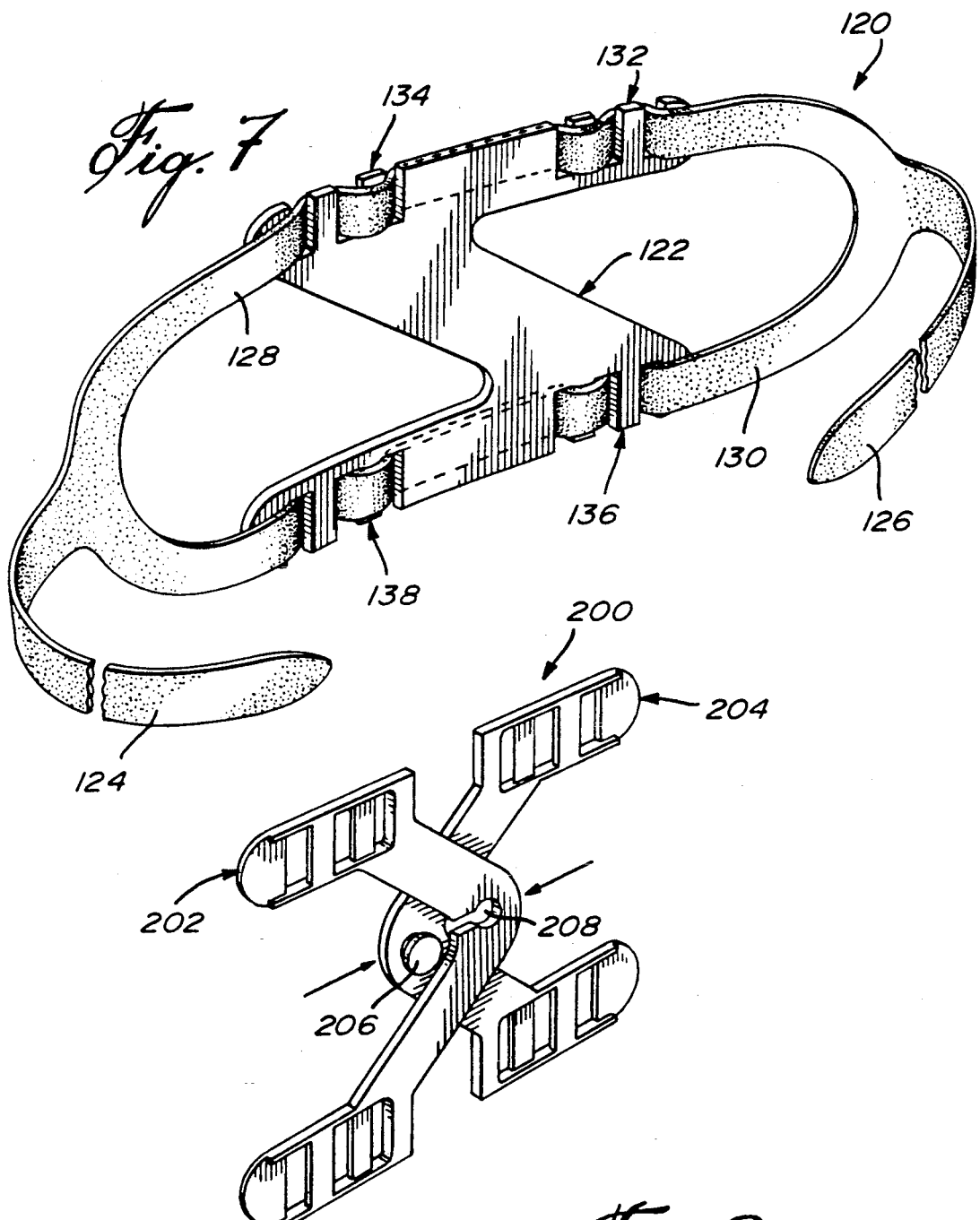

COMBINATION OF A STRAP AND OF A STRAP SPREADER

FIELD OF THE INVENTION

The present invention relates to a strap and spreader combination for use in cooperation with goggles.

BACKGROUND OF THE INVENTION

Sport goggles, and in particular goggles used by swimmers, are provided with straps which are attached to opposite sides of the goggles and which define a pair of band portions that extend over the back of the wearer's head. One of the most annoying problems encountered by swimmers is that the straps tend to slide down the head, seriously destabilizing the goggles and causing discomfort. Further, with swimming goggles, a leak may result, causing swimmers to stop, rinse and reinstall the goggles.

STATEMENT AND OBJECTS OF THE INVENTION

The present invention is concerned with providing a combination of a strap and strap spreader for goggles which avoids the above described problems.

This is achieved by providing a strap spreader which stabilizes the goggles, keeps strap adjustment at the back of the head and disperses pressure over a much larger area of the head.

Hence, the present invention is concerned with a combination of a strap and of a strap spreader wherein the strap is formed of a band having a front portion adapted to be mounted to one side of the goggles and having a rear portion displaying a pair of opposite band portions which are adapted to be mounted to four points of attachment on the spreader, the body of which is shaped to fit the contour of the back of the wearer's head. The four points of attachment are disposed so as to provide a better distribution of the pressure across the head so that the goggles may rest gently on the skin.

In one form of the invention, two straps are used wherein each strap consists of a continuous band with one folded end secured to one side of the goggles and two opposite free ends secured to two points of attachment of the spreader.

In another form of the invention, each strap of a pair consists of a band consisting, at one end thereof, of a single band portion to be attached to the goggles and, at the opposite end thereof, of a pair of spaced parallel portions adapted to be respectively secured to two attachment points.

In another form of the invention, the strap has opposite free ends adapted to be attached to opposite sides of goggles and a rear portion which is split into a pair of parallel band portions which are engaged in the four points of attachment.

In another form of the invention, the body is formed of two separate portions which are interconnectable to one another at an intermediate point thereof.

In a further form of the invention, the body is made of high density polyethylene.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

IN THE DRAWINGS

FIG. 3 is a cross-sectional view taken along lines 3—3 of FIG. 1;

FIG. 4 is a view taken along lines 4—4 of FIG. 1;

FIG. 5 is an enlarged cross-sectional view showing the attachment of a free end of a strap to the spreader;

FIG. 6 is a plan view of another embodiment of a strap which may be used in the combination of the present invention;

FIG. 7 is a perspective view of a further embodiment of a combination of a single strap and of a spreader made in accordance with the present invention; and FIG. 8 is a perspective view of another embodiment of a spreader used with the present invention.

DESCRIPTION OF PREFERRED EMBODIMENT

Figure 1:
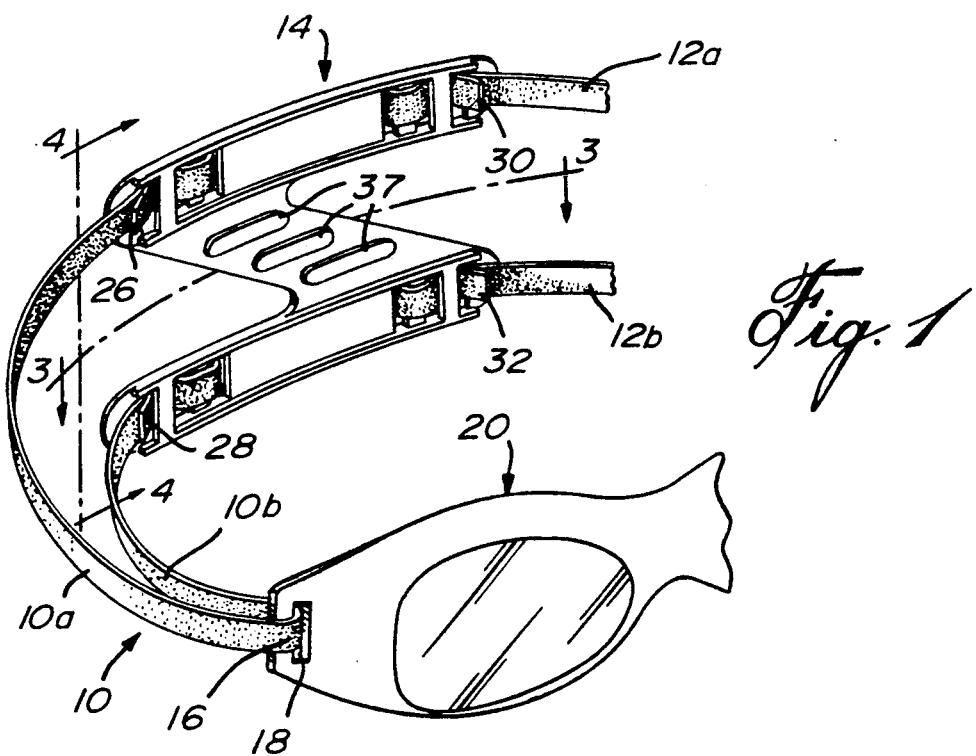
FIG. 1 is a perspective view showing the combination of a pair of straps and of a strap spreader made in accordance with the present invention.
Figure 2:
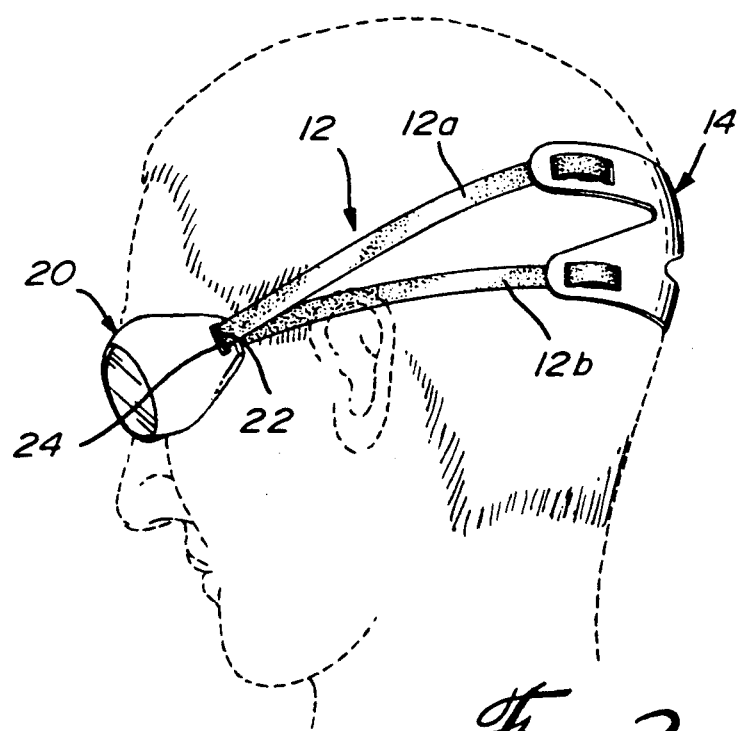
FIG. 2 is a view illustrating the combination mounted on a wearer's head.

Referring to FIGS. 1 and 2, a first embodiment of the invention consists of the combination of a pair of straps 10 and 12 and of a strap spreader 14. The strap 10 has one end 16 folded and engaged in a slot 18 at one side of goggles 20. Similarly, strap 12 is folded at 22 and passes through a slot 24 provided at the opposite side of goggles 20.

The free ends 26 and 28 of band portions 10a and 10b of strap 10 extend through a first pair of attachment points of the spreader 14, each consisting of three successive rectangular openings; similarly, band portions 12a and 12b of strap 12 have their ends 30 and 32 respectively attached to a second pair of attachment points, each also defined by three successive openings.

The straps 10 and 12 are made of an elastic material, such as the one known under the trademark KRATON.

As may be seen in FIGS. 3 and 4, body 14 has a curved shape so as to fit to the contour of the back of the head of a person wearing the goggles. The curvature of the body may be a segment of a spherical, cylindrical or conical shape. Although not shown, the body may also be flat but with sufficient flexibility so that, once placed on the wearer's head, it will fit its contour. The inner face of the body may be formed with a series of projections 37 to limit any slipping of the body once it is positioned on a wearer's head, especially when worn by swimmers using plastic caps.

Preferably, the body is made of plastic material, such as high density polyethylene.

FIG. 5 illustrates the manner in which a strap is mounted at an attachment point of the spreader, one end 28 of a strap being shown received in three successive rectangular openings 40, 42 and 44.

FIG. 6 illustrates another type of strap 110 which may be used with the present invention; it consists of a single band portion 112 which is usually equipped with appropriate attachment means (not shown) to secure it to slots provided at opposite sides of goggles, and of two parallel band portions 114 and 116 which are attached to the body 14 in a manner similar to that of strands 10a, 10b and 12a, 12b shown in FIG. 1.

Referring to FIG. 7, a single strap 120 is shown mounted to a spreader 122. The strap is defined by a pair of opposite front portions 124 and 126 and a rear portion which is split in two parallel band portions 128 and 130 which are curvingly engaged through the four points of attachments 132, 134, 136 and 138 of the spreader. In this embodiment, the three openings of each attachment point are opened edgewise so as to enable easy insert of the strap portions therein.

Referring to FIG. 8, there is shown another embodiment of a spreader 200 which is made in accordance with the present invention. It consists of two separate body sections 202 and 204 which are interconnected at an intermediate section by means of a pin 206 engageable in a slotted opening 208. Each section has a V-shaped configuration, with each extremity being provided with an attachment point formed of three successive openings to receive the straps in a manner similar to that shown in FIGS. 1-5.

Although the invention has been described above relative to various forms, it will be evident to the person skilled in the art that it may be modified and refined in a number of ways. For example, the spreader may have various configurations provided, of course, that it is capable of providing, on opposite sides thereof, two vertically spaced attachment points to receive straps mounted to goggles. Therefore, the present invention should not be limited in interpretation, except by the terms of the following claims.

I claim:

1. A combination of a strap and of a strap spreader for use in cooperation with goggles,
   a) a strap being formed of a band having two front portions, each front portion being adapted to be mountable to one side of a pair of goggles and each having a rear portion displaying an upper and a lower band portion; and
   b) a spreader having a rigid body defining a curved surface adapted to fit the contour of the back of a wearer's head,
   said surface defining vertically spaced upper and lower edges and including, adjacent said edges, on opposite sides of said body, upper and lower receiving means for said upper and lower band portions, which define a point of attachment for each of said upper and lower band portions
   said receiving means maintaining said band portions at a fixed distance from one another when said body is positioned on a wearer's head in combination with said strap and a pair of goggles.

2. A combination as defined in claim 1, wherein the rear band portions of said strap do not join one to another, so that the combination has a pair of straps, each of said straps consisting of a band with a folded front portion securable to one side of the goggles and a pair of opposite upper and lower free rear portions, each of said rear portions being secured to a respective attachment point.

3. A combination as defined in claim 1, comprising a pair of straps, each strap defining, on one side thereof, a single band portions band portion adapted to be mounted to one side of said goggles and, at an opposite side thereof, a pair of parallel band portions adapted to be respectively secured to two of said attachment points.

4. A combination as defined in claim 1, wherein said strap is a single band having opposite front portions adapted to be secured to opposite sides of said goggles and a pair of parallel rear band portions adapted to be engaged in said receiving means.

5. A combination as defined in claim 1, wherein said body is curved and Z-shaped.

6. A combination as defined in claim 1, wherein each said receiving means consists of three adjacent openings in said surface.

7. A combination as defined in claim comprising antislipping means on an inner face of said surface.

8. A combination of a strap and of a strap spreader for use in cooperation with goggles,
   a) a strap being formed of a band having two front portions, each front portion being adapted to be mountable to one side of a pair of goggles and each having a rear portion displaying an upper and a lower band portion; and
   b) a spreader having a rigid body defining a curved surface adapted to fit the contour of the back of a wearer's head,
   said surface defining vertically spaced upper and lower edges and including, adjacent said edges, on opposite sides of said body, upper and lower receiving means for said upper and lower band portions which define a point of attachment, one for each of said upper and lower band portions
   said receiving means maintaining said band portions at a fixed distance from one another when said body is positioned on a wearer's head in combination with said strap and a pair of goggles,
   wherein said body is formed of a pair of interconnected V-shaped sections, each section having a pair of said attachment points adjacent the extremities thereof.

9. A combination as defined in claim 8, wherein one of said sections includes a pin at an intermediate point thereof, said pin being engageable in a slotted opening at an intermediate point of the other of said sections.

10. A combination as defined in claim 6, wherein said body is made of a high density polyethylene.

* * * * *